United States Patent [19]
Pool

[11] Patent Number: 5,894,129
[45] Date of Patent: Apr. 13, 1999

[54] IMAGING APPARATUS

[75] Inventor: Peter James Pool, Essex, United Kingdom

[73] Assignee: EEV Limited, Essex, United Kingdom

[21] Appl. No.: 08/684,259

[22] Filed: Jul. 19, 1996

[30] Foreign Application Priority Data

Jul. 28, 1995 [GB] United Kingdom ............... 9515539

[51] Int. Cl.$^6$ ........................................ G01T 1/24
[52] U.S. Cl. ........................................ 250/370.09
[58] Field of Search ........................................ 250/370.09

[56] References Cited

U.S. PATENT DOCUMENTS

| | | |
|---|---|---|
| 4,694,316 | 9/1987 | Chabbal . |
| 5,053,873 | 10/1991 | Taniji . |
| 5,513,252 | 4/1996 | Blaschka et al. ............... 378/98.8 |
| 5,693,948 | 12/1997 | Sayed et al. ............... 250/370.09 |

FOREIGN PATENT DOCUMENTS

| | | |
|---|---|---|
| 0 593 030 A3 | 4/1994 | European Pat. Off. . |
| 42 17 627 A1 | 12/1993 | Germany . |
| 1601542 | 10/1981 | United Kingdom . |

OTHER PUBLICATIONS

N. G. Loter, P. Burstein, A. Krieger, D. Ross, D. Harrison, D. J. Michaels, "Soft x–ray and XUV imaging with a charge–coupled device (CCD)–based detector, " *Solid State Imagers for Astronomy*, Proc. SPIE vol. 290, pp. 58–61, 1981.
[U.S. Classification: 250/370.09].

*Primary Examiner*—Constantine Hannaher
*Attorney, Agent, or Firm*—VENABLE; Robert J. Frank; Michael A. Sartori

[57] ABSTRACT

In an imaging apparatus particularly for use in intra-oral dental applications, a solid state imager is arranged to detect X-ray radiation from a source after passing through an object. Prior to irradiation by the source, charge accumulated in the elements of a CCD is clocked from two or more rows into a register such that charges are summed. The register is output via a charge amplifier which sums the charge applied to it to give a relatively large output signal which is amplified and applied to thresholder. Onset of X-ray irradiation is detected when the signal applied to the thresholder exceeds a reference level. A start signal is then transmitted to a control unit to cause image acquisition to begin.

14 Claims, 1 Drawing Sheet

IMAGING APPARATUS

FIELD OF THE INVENTION

This invention relates to an imaging apparatus and more particularly to solid state imagers which include radiation sensitive detector elements.

BACKGROUND TO THE INVENTION

It has been proposed to use charge coupled devices (CCDs) and other types of solid state detectors for dental and other medical applications using X-ray irradiation to examine structural features of a patient. The CCD replaces the film used in previous systems and enables real-time imaging to be achieved together with a more controlled lower dosage of X-rays for a given exposure.

In one known arrangement, a CCD is used intra-orally and is electrically connected to an X-ray source. When the X-ray source is energized, a start signal is transmitted along the connecting wire to the CCD and to its control circuitry to begin image acquisition and readout. In other arrangements, the X-ray source and CCD have no physical connection. A supplementary sensor is arranged close to the imaging area of the CCD to detect the onset of X-ray energy. On detection of the incident X-ray energy, the sensor sends a signal to the CCD control circuitry to cause imaging to begin.

In another arrangement, the CCD is continually read-out prior to irradiation by X-rays. A signal derived from the CCD is compared with a reference level. If it exceeds the reference level, the image acquisition phase of the CCD operation is initiated.

The present invention seeks to provide an improved imaging apparatus which is particularly advantageously used for dental X-ray diagnosis where the imager device is located intra-orally. The present invention may also be used in other medical or diagnostic applications and could also be advantageously employed for non-medical applications.

SUMMARY OF THE INVENTION

According to the invention, there is provided an imaging apparatus comprising: a solid state imager device having radiation sensitive detector elements arranged in an array of rows and columns; means for summing together charge from elements in two or more rows to derive an output signal; means for using the output signal to detect when radiation to be imaged is incident on the array; and means for initiating image acquisition when the incident radiation is detected.

Solid state devices, such as CCDs, suffer from the generation of a thermally based signal known as dark current. During a wait period, for example, in an X-ray system before X-ray exposure, the imager device generates dark current which uses signal handling capacity of the device and may even totally fill that capacity leaving no space for signal information. When onset of X-rays begins therefore, the device must be emptied of the charge it holds due to thermal generation.

Dark current approximately doubles every 7° C. in silicon devices, and in dental use, CCDs may be used with an operating temperature of up to 40° C. In the previously known arrangement in which the signal output is compared with a reference level, it is therefore necessary to set this reference at a relatively high level to allow for signals arising from 40° C. dark current and other noise features. If the reference is set too low, a false trigger signal may result causing a failed image and requiring the patient to be subjected to a repeat exposure.

By employing the invention, the image acquisition phase of the imager device may be initiated more promptly than the previously known arrangement in which signal clocked from the detector elements prior to irradiation with X-rays is compared with a threshold level. Summing the charge in two or more rows in accordance with the invention provides a signal of higher magnitude than would otherwise be the case. The summing process is essentially noise free. Thus, the signal to noise ratio of the signal is enhanced, and the sensitivity is improved. Preferably, the means for summing includes a register into which charge is successively transferred from the two or more rows to sum the charge, and means is also included for reading out the summed charge from the register. Additionally, the means for summing advantageously includes means for adding together the summed charge stored in different cells of the register. Thus the resultant summed signal may be derived from charge from several rows and columns.

Some or all of the rows of the array may be used to produce the summed charge from which the output signal is derived. The number selected depends on the level of signal required to give the desired sensitivity and the time taken to clock the accumulated charge into the register.

The invention is particularly advantageously used for X-ray irradiation of patients for dental and other medical uses, such as mammography, as it allows X-ray dosages to be reduced to the minimum level required. The dosage of X-ray radiation to which the patient is subjected is minimized as image acquisition is started nearer the beginning of the X-ray pulse. Stringent health and safety requirements specify that unnecessary exposure to X-ray radiation should be avoided, and use of the invention enable these conditions to be met.

Although the invention is particularly useful for dental applications other medical and non-medical applications may also advantageously employ the invention. The invention may be used in X-ray systems or with other types of high energy radiation.

BRIEF DESCRIPTION OF THE DRAWING

One way in which the invention may be performed is now described with reference to the accompanying drawing in which the sole FIGURE schematically illustrates an X-ray imaging arrangement for intra-oral dental use in accordance with the invention.

DESCRIPTION OF A PREFERRED EMBODIMENT

Figure 1:
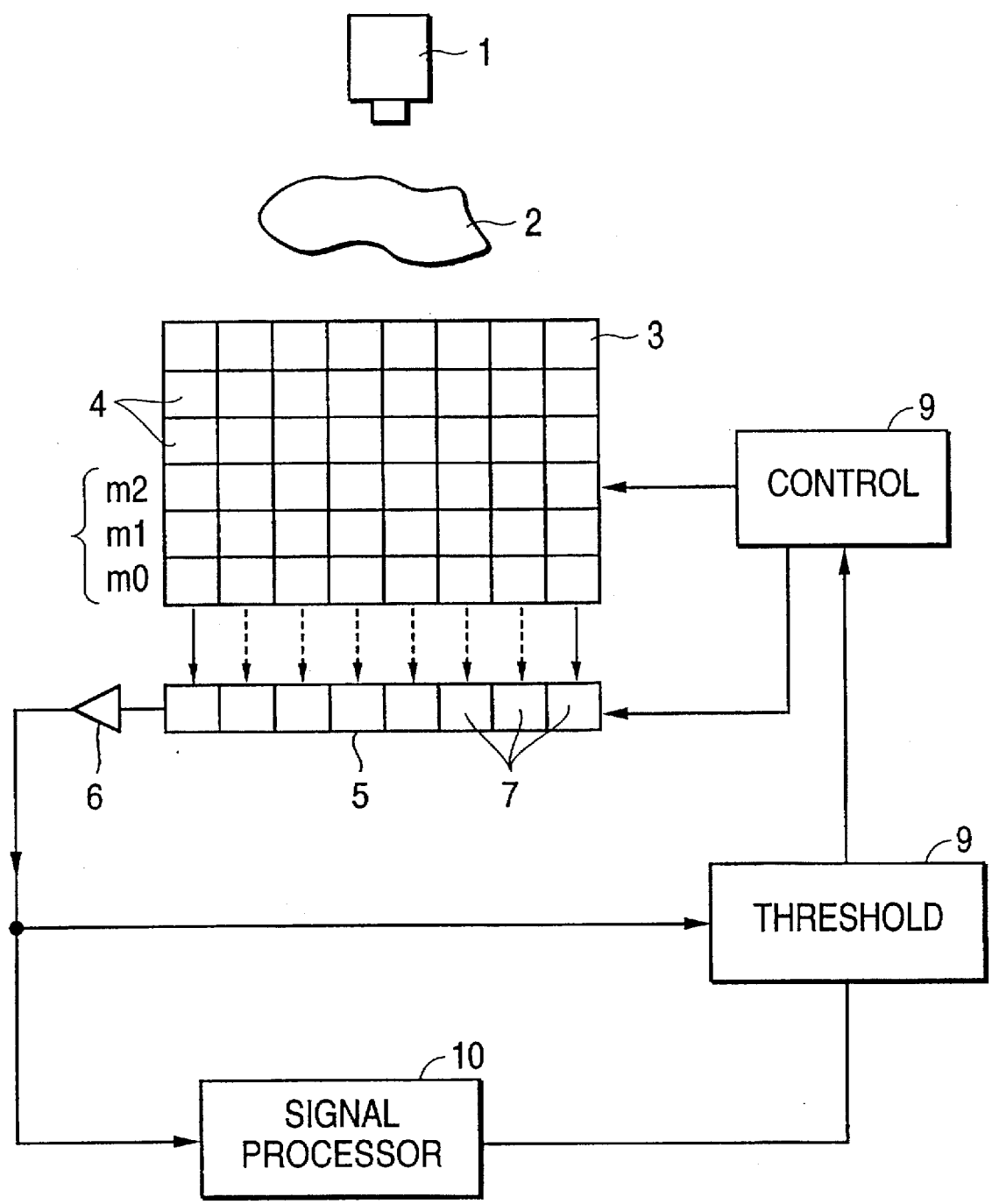

With reference to the FIGURE, an X-ray source 1 is arranged to irradiate a tooth or other object 2 to be imaged behind which is located a CCD. The CCD 3 comprises an array of radiation sensitive detector elements 4 set out in an array of rows and columns, an output register 5, and a charge amplifier 6. The detector elements accumulate charge depending on the intensity of the radiation which is incident on them.

The output register 5, having charge storage cells 7 corresponding in number to the number of columns in the array, is arranged to receive charge clocked out of elements 4 on a row by row basis. A control unit 8 applies appropriate control signals to the electrodes of the arrangement to implement transfer of the charge.

The output of the register 5 is connected via the amplifier 6 to a thresholder 9. A signal processing circuit 10 is arranged to receive signals from the register 5.

During a standby period before irradiation of the object 2 by the X-ray source 1, dark current results in charges accumulating in the elements 4 of the CCD 3. In this arrangement, three rows of charge m0, m1 and m2 are successively clocked into respective cells 7 of the register 5 under the control of control unit 8. The charge in each cell 7 is thus a summation of charge accumulated in three elements of a corresponding column. Once the three rows have been transferred into the register 5, the output is applied to the amplifier 6. In another embodiment a different number of rows may be summed.

The thresholder 9 compares the signal derived from the elements 4 with a threshold level. Prior to irradiation by the X-ray source 1, the signal does not exceed the threshold level and the CCD 3 is kept in standby mode. When X-ray radiation impinges on the radiation detector elements 4, the charge in these elements rapidly increases. The summed charge from the register 5 applied via amplifier 6 is then larger than the threshold level. When this condition is detected at a thresholder 9, a start signal is transmitted to the control unit 8 to begin the image acquisition process of the CCD. Also, the signal processing circuit 10 receives image information from the CCD 3 for signal processing.

In other embodiments of the invention, charge stored in each of the cells 7 may be summed together at the amplifier 6 to produce a high output signal.

In another embodiment of the invention, charge may be summed in both rows and columns to further improve sensitivity.

I claim:

1. Imaging apparatus comprising:

a solid state imager device having radiation sensitive detector elements arranged in an array of rows and columns, each element having a charge;

means for summing charge from elements in at least two rows to derive an output signal;

means for detecting when imaging radiation is incident on said array by using the output signal from said means for summing; and means for initiating image acquisition when said means for detecting detects imaging radiation incident on said array.

2. Apparatus as claimed in claim 1 wherein said means for summing comprises:

a register for receiving the charge transferred from said at least two rows and summing the charge to obtain a summed charge; and means for reading out the summed charge from said register.

3. Apparatus as claimed in claim 2 wherein said register comprises a plurality of cells, and said means for summing further comprises means for adding the summed charge stored the cells of said register.

4. Apparatus as claimed in claim 1 wherein said means for detecting comprises means for applying a threshold test to said output signal from said means for summing.

5. Apparatus as claimed in claim 1 wherein said solid state imager device is a charge-coupled device.

6. Apparatus as claimed in claim 1 wherein said solid state imager device is sensitive to X-ray radiation.

7. Apparatus as claimed in claim 6 further comprising a source of X-ray radiation arranged to irradiate an object located between said imager device and said source of X-ray radiation.

8. A dental X-ray arrangement including imaging apparatus comprising:

a solid state imager device having radiation sensitive detector elements arranged in an array of rows and columns, each element having a charge;

means for summing charge from elements in at least two rows to derive an output signal;

means for detecting when imaging radiation is incident on said array by using the output signal of said means for summing; and means for initiating image acquisition when said means for detecting detects imaging radiation incident on said array.

9. Arrangement as claimed in claim 8 wherein said dental X-ray arrangement is an intra-oral dental X-ray arrangement, and said solid state imager device is a charge-coupled device.

10. An imaging apparatus comprising:

an array of detector elements arranged in rows and columns and for receiving a radiation image, each detector element storing a charge;

a register having a plurality of charge storage cells coupled to said array, each charge storage cell coupled to a column of said array and for accumulating charges from a plurality of detector elements in the column coupled to the storage cell to obtain a summed charge; and a processing unit coupled to said register for receiving the summed charges from the plurality of charge storage cells of said register and for determining whether the radiation image has been transmitted to said array.

11. An imaging apparatus as in claim 10, wherein said processing unit comprises a threshold unit for comparing the summed charges from the plurality of charge storage cells to a threshold for determining whether the radiation image has been transmitted to the array.

12. An imaging apparatus as in claim 10, wherein said processing unit comprises:

a summing unit for summing the summed charges from the plurality of charge storage cells to obtained a total summed charge; and a threshold unit for comparing the total summed charge from the summing unit to a threshold for determining whether the radiation image has been transmitted to the array.

13. An imaging apparatus as in claim 10, wherein said imaging apparatus is an intra-oral dental imaging apparatus, and said array is a charge-coupled device.

14. An imaging apparatus as in claim 10, further comprising:

a control unit coupled to said processing unit and said array for initiating radiation image acquisition by said array when said processing unit determines that the radiation image has been transmitted to said array.

* * * * *